United States Patent [19]
Dewaele

[11] Patent Number: 5,985,140
[45] Date of Patent: Nov. 16, 1999

[54] REDUCTION IN BACK PRESSURE BUILDUP IN CHROMATOGRAPHY BY USE OF GRADED FILTER MEDIA

[75] Inventor: Chris Dewaele, Nazareth, Belgium

[73] Assignee: Bio-Rad Laboratories, Inc., Hercules, Calif.

[21] Appl. No.: 09/138,434

[22] Filed: Aug. 21, 1998

[51] Int. Cl.[6] .................................................. B01D 15/08
[52] U.S. Cl. ......................... 210/198.2; 210/656; 96/101
[58] Field of Search .................... 210/635, 656, 210/658, 659, 198.2, 456; 95/82, 85; 96/101, 105

[56] References Cited

U.S. PATENT DOCUMENTS

| | | | |
|---|---|---|---|
| 4,283,280 | 8/1981 | Brownlee | 210/198.2 |
| 4,399,032 | 8/1983 | Mott | 210/198.2 |
| 4,563,275 | 1/1986 | McEachern | 210/198.2 |
| 4,582,608 | 4/1986 | Ritacco | 210/198.2 |
| 4,637,877 | 1/1987 | Hartmann | 210/347 |
| 4,882,047 | 11/1989 | Shalon | 210/198.2 |
| 4,902,420 | 2/1990 | Pall | 210/346 |
| 5,013,433 | 5/1991 | Shalon | 210/198.2 |
| 5,100,551 | 3/1992 | Pall | 210/346 |
| 5,854,431 | 12/1998 | Linker | 73/863.23 |

*Primary Examiner*—Ernest G. Therkorn
*Attorney, Agent, or Firm*—Townsend and Townsend and Crew LLP

[57] ABSTRACT

Cartridges for high performance liquid chromatography are designed for use with a large number of repeated injections without excessive buildup of back pressure by the inclusion of a filter medium consisting of sintered stainless steel fibers formed into a non-woven structure whose pore size decreases in the direction of flow down to a pore size of less than ten microns.

7 Claims, 1 Drawing Sheet

REDUCTION IN BACK PRESSURE BUILDUP IN CHROMATOGRAPHY BY USE OF GRADED FILTER MEDIA

BACKGROUND OF THE INVENTION

This invention relates to column chromatography, and in particular to columns designed to separate components of whole blood.

Chromatography in general and high-performance liquid chromatography (HPLC) in particular are widely used for analytical and preparative separations of mixtures of chemical species. The columns used for HPLC are typically used for a series of successive analyses, particularly in automated chromatographic systems, and in general where the repeated use of a single column permits direct sample-to-sample comparisons without the error that is introduced by cleaning the separatory resin between injections or by exchanging one column for a fresh column of the same composition. Solid debris often enters these columns, having been entrained by the sample or the carrier fluid, and accumulates in the column, obstructing the free flow of fluid and causing back pressure to rise. The debris arises from several sources. Whole blood, for example, either diluted or undiluted, contains cell wall fragments and other insoluble matter. Included among this insoluble matter are insoluble proteins as well as soluble proteins that agglomerate and/or precipitate. Another source is the chromatographic instrument itself. Components of the instrument such as valves and pump seals tend to disintegrate and release particulate matter into the carrier fluid.

Debris from all of these sources tend to clog the column, inhibiting the free flow of liquid through the column and causing the back pressure to rise. Metal frits are usually present in the column to hold the resin, and these frits act as filters for the solid debris, but the frits themselves become clogged with the debris, again causing the column back pressure to rise. One of the sites where flow blockage occurs is the interface between the frit and the resin, since the contact between the frit and the resin reduces the sizes of the interstitial spaces in the interfacial region, rendering them narrower than those of either the frit or the resin themselves. The spaces at the interfacial region are small enough to block even the passage of very small proteinaceous material. This not only causes back pressure to rise but also interferes with the separation when these proteins are among the components sought to be identified and/or quantified.

Some of the debris can be removed by filtration or centrifugation that is off-line (i.e., before injection into any continuous-flow column system). This is a time-consuming step, however, and provides an added source of operator error. For on-line systems (i.e., automated, continuous-flow systems), guard columns and prefilters that are not in direct contact with the resin have been included, but for the reasons set forth in the preceding paragraph, back pressure still rises with repeated injections. The rising back pressure typically requires that the guard columns be replaced after 50 to 200 injections, depending on the application.

SUMMARY OF THE INVENTION

A highly effective filter medium has now been discovered for removing debris present in chromatographic samples and carrier fluids. The filter medium removes the debris and yet permits the passage of many more samples than filters of the prior art. The filter medium is a multi-layered structure of non-woven sintered fibers of stainless steel, the fibers being progressively more densely packed in the direction of flow. This results in progressively decreasing pore sizes which are the interstitial spaces between the fibers. The decrease in interstitial clearance may be attributable to a greater number of fibers per unit volume or to the use of fibers of a progressively smaller diameter. Most conveniently, however, fibers of a single diameter are used, and the variation is created by stepwise changes in the packing density of the fibers. In any event, the interstitial clearance reduces to a very small diameter sufficient to retain the debris associated with whole blood and yet the filter medium has a greatly reduced tendency to clog.

A surprising effect of the use of a filter medium of this description is that it can be placed in direct contact with a separatory resin without creating an interfacial region of reduced pore size. This is of particular value in the analysis of samples of whole blood, since it allows the blood proteins of small size to pass through from the filter medium to the resin without causing an increased blockage at the interface between the filter medium and the resin. In addition to whole blood samples, however, the present invention is applicable to analytical and preparative samples in general that have a tendency to cause a gradual increase in back pressure in a chromatographic column after repeated injections through the column.

BRIEF DESCRIPTION OF THE FIGURE

The FIGURE attached hereto is an exploded view in cross section of an HPLC cartridge incorporating a filter medium in accordance with the present invention.

DETAILED DESCRIPTION OF THE INVENTION AND PREFERRED EMBODIMENTS

Figure 1:
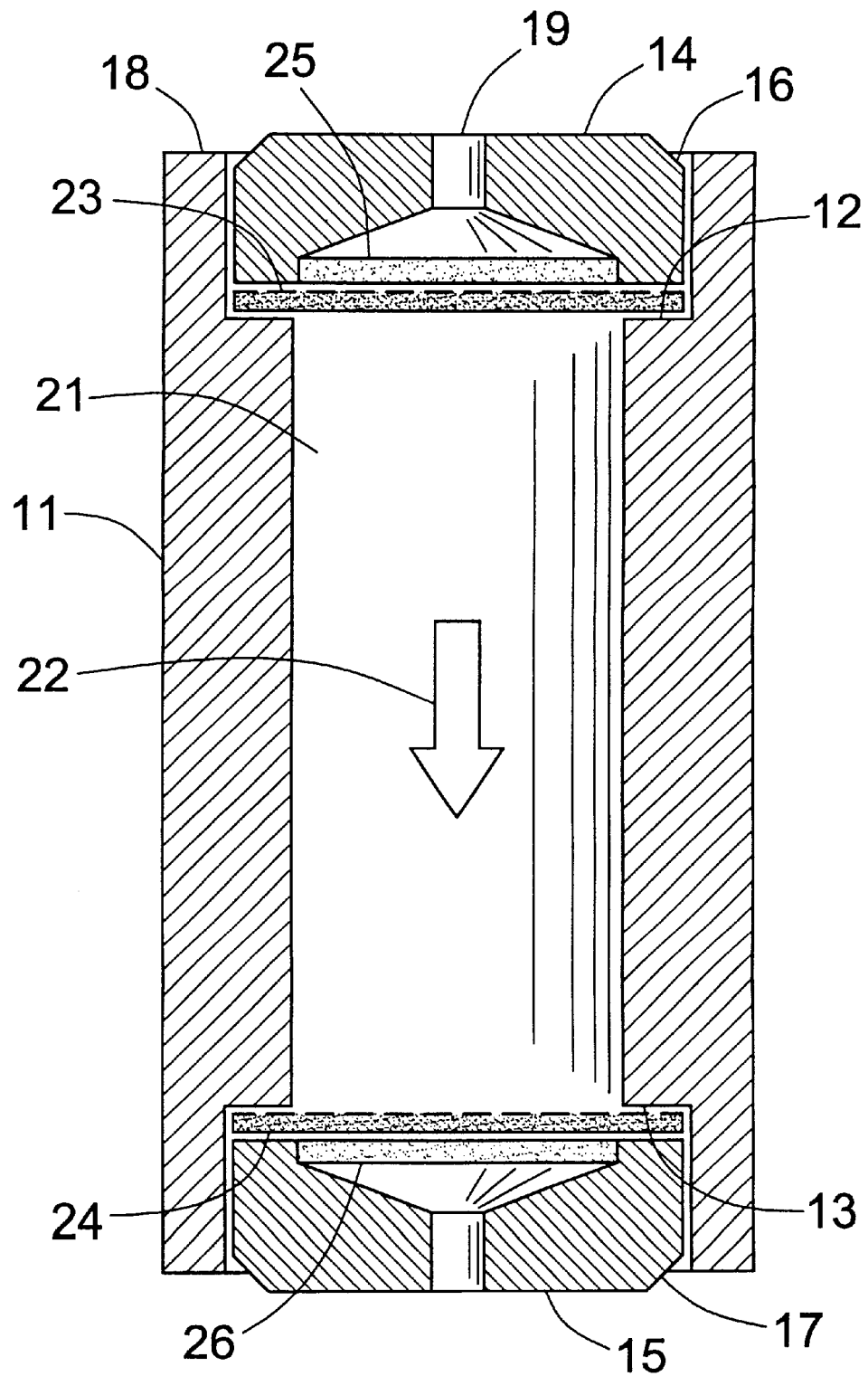

The gradation of the pore size is oriented so that the debris-containing sample fluid enters the filter through the side with the larger interstitial spaces, passes through the filter, and leaves the filter through the side with the smaller interstitial spaces. The degree and spatial rate of gradation of size may vary within the scope of this invention, as may the pore sizes themselves. Best results however will be obtained with a pore size gradation that decreases to an ultimate size (on the downstream side of the filter) that is narrow enough to retain particles that are 10 microns in diameter, preferably 5 microns in diameter, and most preferably 1 to 3 microns in diameter.

Other relevant factors of the filter are its thickness and permeability factor, both of which may range as may the pore size. The thickness in most cases will be within the range of from about 0.1 mm to about 1.0 mm, preferably from about 0.2 mm to about 0.6 mm, and most preferably from about 0.3 mm to about 0.6 mm. The permeability factor k is defined by Darcy's Law:

$$\frac{\Delta P}{L} = \frac{\mu}{k} V$$

where $\Delta P$ is the pressure drop, L is the thickness of the filter, $\mu$ is the fluid viscosity, and V is the superficial velocity. The permeability factor in most cases will be within the range of from about $4\times10^{-13}$ to about $1\times10^{-10}$ m$^2$, preferably from about $4\times10^{-13}$ to about $1\times10^{-11}$ m$^2$, and most preferably from about $4\times10^{-13}$ to about $4\times10^{-12}$ m$^2$.

The gradation may be stepwise or continuous, and the variation from the larger-pore side to the small-pore side may vary widely. The pore size differential (i.e., the difference between the largest pore size and the smallest pore size)

may thus range from about 1 micron to about 50 microns, or preferably from about 2 microns to about 20 microns. In filter media will stepwise gradations, the filter will contain two or more gradations, preferably three to six, and the pore size on the course (upstream) side of the filter (the coarsest portion of the filter) may range from about 2 microns to about 50 microns, preferably from about 2 microns to about 6 microns.

The filter material is sintered non-woven stainless steel fibers. The particular stainless steel is not critical to the invention, and a variety of different stainless steel alloys can be used. Austenitic stainless steels, i.e., those whose chief alloying elements are chromium and nickel, are preferred. A particularly preferred stainless steel is 316L stainless steel, whose composition is approximately 0.03% carbon, 2.00% manganese, 1.00% silicon, 16.0–18.0% chromium, 10.0–14.0% nickel, 0.45% phosphorus, 0.03% sulfur, and 2.0–3.0% molybdenum (all percents by weight). Examples of other useful stainless steels are 304, 304H, 304L, 304 LN, 316, 316F, 316H, 316LN, 316N, 317, 317L, 321, 321H, 347, 347H, 348, 348H, and 384.

A currently preferred filter medium that meets the parameters of this invention is BEKIPOR® ST filter medium, and in particular BEKIPOR® ST 3AL3, a product of NV Bekaert SA of Belgium, available through Bekaert Fibre Technologies Europe, Zwevegem, Belgium, and Bekaert Corporation, Atlanta, Ga., USA. This medium is made of 316L stainless steel fibers, randomly compressed in a non-woven structure and sintered, and is supplied in sheets, with typical lateral dimensions of 1180 mm×1500 mm and 0.35 mm in thickness. This particular product has an absolute filter rating of 3 microns, a bubble point pressure of 12,300 Pa (ASTM E 128061, equivalent ISO 4003), an average air permeability of 9 L/dm$^2$/min at 200 Pa (NF A 95-352, equivalent IOS 4022), a permeability factor k of $4.80 \times 10^{-13}$, a weight of 975 g/m$^2$, a porosity of 65%, and a dirt holding capacity of 6.40 mg/cm$^2$ according to Multipass method ISO 4572 with 8" initial differential pressure. Other media of similar characteristics and made of similar materials can also be used.

In accordance with this invention, the filter media are incorporated into cartridges used for HPLC or other forms of chromatography. An example of such a cartridge is shown in a longitudinal exploded cross section in the attached drawing. The cartridge consists of a hollow cylindrical tube 11, generally of metal such as stainless steel, and open at each end. The interior of each end of the tube has a shoulder 12, 13 extending around the circumference of the inner tube surface. End plugs 14, 15 fit in each end of the tube, resting on the shoulders. Each end plug terminates in a frustum 16, 17, so that the plug can be sealed into the end of the tube by a rolling tool which curves the end edge 18 of the tube inward over the frustum, compressing the end plug against the shoulder to seal the end plug in place and seal the end of the tube closed except for a narrow orifice 19 in the end plug that permits passage of the sample. The interior portion 21 of the cylindrical tube between the shoulders is a chamber for retaining the column packing used as a chromatographic separation medium, and the intended direction of flow of the sample and carrier fluid through the cartridge is indicated by the arrow 22.

Bordering the separation medium chamber 21 at both the upstream and downstream ends are disks 23, 24 of the sintered non-woven stainless steel fiber filter medium described above. While this particular embodiment contains such a disk at each end of the chamber, the cartridge may also contain a single such disk at the inlet (upstream) end only. In either case, in view of the gradation of pore size in each filter medium, the flow direction is significant, and the disks are oriented such that the side with the larger pore size is at the upstream side relative to the flow direction. As sheets of the filter medium are supplied by commercial suppliers of the medium, the side with the larger pore size is frequently differentiated by being colored or otherwise marked to guide the user in obtaining the desired orientation. In the drawing, the side with the larger pore size is indicated by a dashed line on each filter medium disk. Since the filter medium is thin and flexible, mechanical support is preferably provided to assure that the filter medium remains flat. The mechanical support can be provided by another porous sintered stainless steel disk 25, 26, a perforated metal plate, or an equivalent structure. Only the filter medium itself 23, 24, however, contacts the resin.

Once assembled, the cartridge is mounted into a cartridge holder in a chromatography apparatus. Such holders are widely used in on-line chromatography systems, are well known to those skilled in the art, and are readily available from suppliers of HPLC equipment. Examples of suitable cartridge holders are those described in McEachem, U.S. Pat. No. 4,563,275, issued Jan. 7, 1986, and Brownlee, U.S. Pat. No. 4,283,280, issued Aug. 11, 1981, both of which are incorporated herein by reference.

The foregoing is offered primarily for purposes of illustration. It will be readily apparent to those skilled in the art that the materials, dimensions, usages, and other parameters of the system described herein may be further modified or substituted in various ways without departing from the spirit and scope of the invention.

I claim:

1. In a chromatography column cartridge comprising:
   a rigid cylindrical tube defining a separatory resin chamber and a direction of flow of carrier fluid therethrough,
   a pair of resin-retaining, liquid-diffusing screens, one said screen bordering said chamber at an upstream end thereof and the other bordering said chamber at a downstream end thereof, and
   a pair of end plugs, one seated within each end of said cylindrical tube, the improvement in which said screen bordering said chamber at said upstream end is a filter of sintered, non-woven stainless steel fibers of graded interstitial passages decreasing in size in said direction of flow.

2. A chromatography column in accordance with claim 1 in which said graded insterstitial passages decrease to a minimum size that is narrow enough to retain particles 10 microns in diameter.

3. A chromatography column in accordance with claim 1 in which said graded insterstitial passages decrease to a minimum sized that is narrow enough to retain particles 5 microns in diameter.

4. A chromatography column in accordance with claim 1 in which said graded insterstitial passages decrease to a minimum sized that is narrow enough to retain particles 1 microns to 3 microns in diameter.

5. A chromatography column in accordance with claim 1 in which said graded insterstitial passages decrease to a minimum size that is narrow enough to retain particles 10 microns in diameter, and said screen has a thickness of from about 0.1 mm to about 1.0 mm and a permeability factor of from about $4 \times 10^{-13}$ to about $1 \times 10^{-10}$ m$^2$.

6. A chromatography column in accordance with claim 1 in which said graded insterstitial passages decrease to a minimum size that is narrow enough to retain particles 5 microns in diameter, and said screen has a thickness of from about 0.2 mm to about 0.6 mm and a permeability factor of from about $4 \times 10^{-13}$ to about $1 \times 10^{-11}$ m$^2$.

7. A chromatography column in accordance with claim 1 in which said graded fiber diameter decrease to a minimum size that is narrow enough to retain particles 1 microns to 3 microns in diameter, and said screen has a thickness of from about 0.3 mm to about 0.6 mm and a permeability factor of from about $4 \times 10^{-13}$ to about $4 \times 10^{-12}$ m$^2$.

* * * * *